United States Patent

Cosentino et al.

Patent Number: 5,766,480
Date of Patent: Jun. 16, 1998

[54] METHOD FOR PRIMING A HOLLOW FIBER OXYGENATOR

[75] Inventors: Louis C. Cosentino, Deephaven, Minn.; John E. Briddon, Maastright, Netherlands; Richard P. Goldhaber, Wayzata; Paul H. Hess, Plymouth, both of Minn.

[73] Assignee: Minntech Corporation, Minneapolis, Minn.

[21] Appl. No.: 730,443

[22] Filed: Oct. 15, 1996

[51] Int. Cl.$^6$ .............. B01D 65/00; B01D 63/02; A61M 1/36

[52] U.S. Cl. .............. 210/644; 210/175; 210/180; 210/188; 210/321.79; 210/321.8; 210/321.88; 210/321.89; 210/645; 422/44; 422/45; 422/46; 604/4; 604/122

[58] Field of Search .............. 210/644, 645, 210/150, 175, 180, 188, 321.79, 321.8, 321.88, 321.89; 422/44, 45, 46; 604/4, 122

[56] References Cited

U.S. PATENT DOCUMENTS

| | | | |
|---|---|---|---|
| 5,039,482 | 8/1991 | Panzani et al. | 422/46 |
| 5,137,531 | 8/1992 | Lee et al. | 422/46 |
| 5,429,184 | 7/1995 | Bach et al. | 422/46 |

*Primary Examiner*—John Kim
*Attorney, Agent, or Firm*—Barbara A. Wrigley

[57] ABSTRACT

A method is provided for priming a hollow fiber oxygenator which is integrated with a hollow tube heat exchanger. A closed priming circuit is created between a cardiosurgery reservoir, the combined hollow fiber oxygenator and heat exchanger and a vacuum source. Vacuum pressure is applied to the closed priming circuit to evacuate the residual air from the circuit. Priming solution is released from the cardiosurgery reservoir and fills the evacuated closed priming circuit.

8 Claims, 2 Drawing Sheets

METHOD FOR PRIMING A HOLLOW FIBER OXYGENATOR

FIELD OF THE INVENTION

This invention relates to the field of priming hollow fiber membrane type oxygenators. In particular, it relates to a quick and efficient method of priming hollow fiber oxygenator integrated with a hollow tube heat exchanger which allows for rapid and efficient priming of the oxygenator heat exchanger included in an extracorporeal circuit during cardiosurgery.

DESCRIPTION OF THE RELATED ART

From the first operation to repair a heart in 1891 until the early 1950s, heart surgeons were limited by the problem of trying to work on the heart while it was still beating. The heart's constant motion, and the presence of blood that obscured the surgeon's view, made repairing heart defects a surgical challenge. Surgeons had to work quickly and there was always a danger of disrupting blood circulation to vital organs. The solution to this problem came in the late 1950s with the development of the first oxygenators.

In nature, deoxygenated blood from the veins returns to the heart's right atrium. From the right atrium, blood is pumped to the right ventricle, then through the pulmonary artery to the lungs. The lung oxygenates the blood while removing carbon dioxide as it passes through the lung's alveolar capillary network. Oxygenated blood is then returned to the left atrium by way of the pulmonary veins. Blood is then pumped through the mitral valve into the left ventricle and pumped back into the body's circulatory system. Cells are replenished with oxygen and carbon dioxide is taken up by the blood as the blood passes through the body's capillary system. After this gaseous exchange is accomplished, the blood is returned to the heart and the cycle is repeated.

During cardiopulmonary surgery, venous blood is taken from the patient's circulation by means of a canula placed in the vena cavae. The blood "bypasses" the heart and lungs and enters what is referred to as the "extracorporeal circuit" or literally a circuit "outside the body." Oxygenation of the patient's blood takes place in an oxygenator much in the same way as it does in the natural process. After the blood is oxygenated and temperature regulated, it is returned to the patient's arterial circulation through a cannula so that the patient's body may utilize the oxygenated blood.

Prime Volume

Prime volume is the volume of liquid that the surgeon pumps through the extracorporeal system to "prime" it. Typically, prior to the initiation of surgery the total internal volume of the extracorporeal circuit, which includes the oxygenator, cardioplegia line, ventricular vent line, etc., must be primed. Priming is done to flush out any extraneous gas from the extracorporeal circuit prior to the introduction of the blood. The larger the priming volume, the greater the amount of priming solution present in the circuit which mixes with the patient's blood. The mixing of the blood and priming solution causes hemodilution. Hemodilution is disadvantageous and undesirable because the relative concentration of red blood cells must be maintained during the operation in order to minimize adverse effects to the patient.

In order to reduce the deleterious effects of hemodilution donor blood may be used. However, the use of donor blood is undesirable because while it reduces the disadvantages associated with hemodilution, donor blood presents complications such as compatibility and the potential transmission of disease. Alternatively, one may use hemoconcentrators to counter the effects of hemodilution. However, such devices add an additional cost to the procedure thus increasing an already expensive operation.

Another disadvantage of large prime volumes is the amount of time expended by the perfusionist in priming the circuit, which in turn increases the start-up time for surgery while operating personnel stand-by. The great majority of commercially available oxygenators have large prime volumes. Typically, the prime volume of the total extracorporeal circuit ranges from two to two and a half liters. Of that volume, the prime liquid in some commercially available oxygenators ranges from 550 mL to 750 mL such as that disclosed in U.S. Pat. No. 5,137,531 to Lee. It would be an advantage over commercially available oxygenators to provide an oxygenator that has a markedly reduced prime volume in order to overcome the disadvantages of commercially available, large prime units.

Reducing prime volume, however, affects other performance characteristics as well. For example, if prime is decreased by removing gas transfer fibers, oxygen transfer decreases, and the pressure drop decreases. If prime is decreased by increasing the pack density of the gas exchange fibers, oxygen transfer will increase, heat exchange efficiency will probably not be affected, but pressure drops will increase dramatically. If prime is decreased by reducing the available surface area of the heat exchange unit, oxygen transfer will not be affected but heat exchange efficiency will decrease. Therefore, one must carefully choose the design characteristics that will provide an oxygenator with a low prime volume, high oxygen transfer rates, high heat exchange efficiency and low pressure drops.

Priming Procedure

As stated above, prior to initiating the cardiosurgery procedure, the entire extracorporeal circuit must be primed with a hemocompatible fluid, such as sterile saline, so that all the air which may be trapped within the extracorporeal circuit is removed. This has been typically accomplished by forcing, typically using gravity forces only, or pumping the priming fluid through the extracorporeal circuit. This "pushes" the trapped air out of the circuit, including a combined hollow fiber oxygenator heat exchanger. A majority of priming procedures require vigorous "tapping" of the oxygenator to dislodge trapped air from within the device. Any air which may remain within the circuit during the cardiosurgery procedure causes decreased performance during the operation.

For example, the patient's blood may not be sufficiently oxygenated as it passes through the oxygenator. In hollow fiber type oxygenators, the oxygen flows through the lumens of the hollow fibers while the blood flows on the exteriors. Blood is oxygenated because of the oxygen concentration gradient that exists between the oxygen gas present in the hollow fiber lumens and the blood surrounding the exterior of the fiber. High oxygen transfer rates are desirable to make as much oxygen available to the patient's system as possible. Air bubbles which may remain in the oxygenator, usually between the exterior surfaces of the hollow fibers, will direct blood flow around the air bubbles thereby decreasing the amount of hollow fiber surface area available for blood contact and, therefore, efficient gas exchange.

Another example of the consequence possible due to residual air in the extracorporeal circuit is the increased potential for high pressure drop within the hollow fiber oxygenator. Pressure drop is the pressure differential between the blood inlet and the blood outlet port and measures the force that literally pushes the blood through the blood pathway of the oxygenator. Any air remaining in the combined hollow fiber oxygenator heat exchanger may interact with blood components. It is theorized that such interaction may activate the compliment cascade or other thrombogenic factors which then causes the blood to coagulate or clot. These clots adhere to the interior surfaces of the combined hollow fiber oxygenator heat exchanger causing maldistribution of the blood flow through the device. High pressure drop, i.e. high oxygenator inlet pressure, has been associated with this "clotting" phenomenon. High pressure drops stress component parts and connections of the oxygenator. High pressure drops may necessitate the replacement of the oxygenator, or the combined oxygenator heat exchanger, during surgery which increases both time and expense of the surgical procedure.

Accordingly, there is a need for a rapid and more efficient method for priming a hollow fiber oxygenator heat exchanger to reduce the priming time and to more effectively remove air from the extracorporeal circuit including a combined hollow fiber oxygenator heat exchanger.

SUMMARY OF THE INVENTION

It is an object of the method for priming a combined hollow fiber oxygenator heat exchanger in accordance with the present invention to solve the problems outline above that have heretofore inhibited attaining rapid priming and efficient air removal in an extracorporeal circuit including a combined hollow fiber oxygenator heat exchanger.

The method for priming a combined hollow fiber oxygenator heat exchanger in accordance with the present invention includes (a) creating a closed priming circuit within a extracorporeal circuit wherein (i) a cardiosurgery reservoir outlet is in fluid communication with a venous blood inlet of a hollow fiber oxygenator heat exchanger, and (ii) an arterial blood outlet of the hollow fiber oxygenator heat exchanger is in fluid communication with a venous blood inlet port of a cardiosurgery reservoir; (b) providing a sufficient volume of a priming fluid in the cardiosurgery reservoir to fill an internal volume of the closed priming circuit; (c) providing a vacuum source to a gas inlet of the hollow fiber oxygenator heat exchanger; (d) applying vacuum pressure from a vacuum source to the closed priming circuit for a sufficient amount of time creating an evacuated closed priming circuit; (e) releasing the priming fluid within the cardiosurgery reservoir to thereby prime the evacuated closed priming circuit; and (f) recirculating the priming solution through the closed priming circuit until attachment of the extracorporeal circuit to a patient's circulatory system.

One advantage of the method of the present invention is to reduce the time required for pre-operative set up by reducing the priming time. Another advantage of the present invention is to decrease the potential for high pressure drop during the cardiosurgery procedure and, thus, reducing the likelihood of a device change out.

DETAILED DESCRIPTION OF THE PRESENTLY PREFERRED EXEMPLARY EMBODIMENT

A. The Priming Circuit

Figure 1:
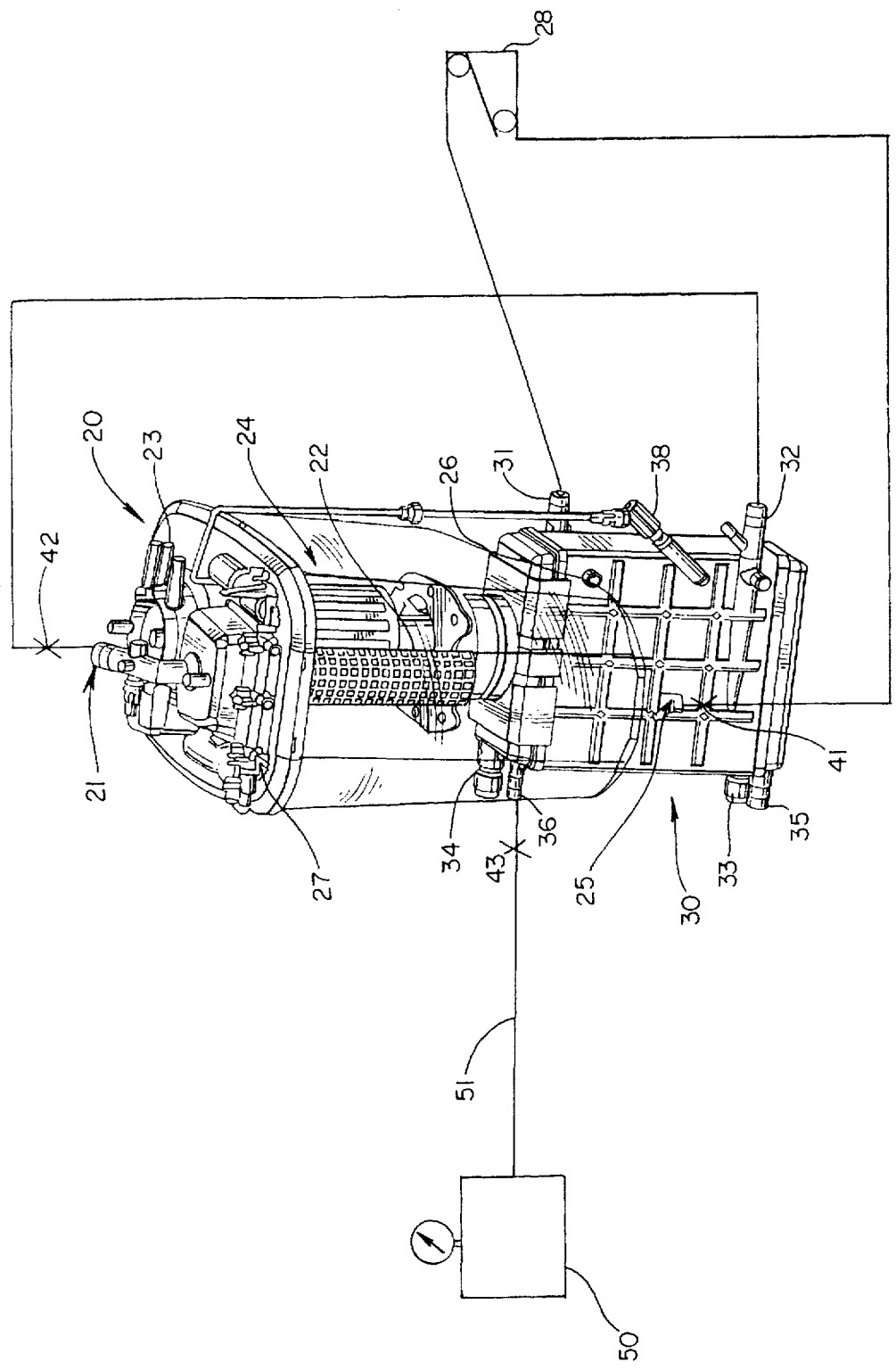
FIG. 1 is a pictorial view of a closed priming circuit in accordance with the method of the present invention, including a hollow fiber oxygenator heat exchanger in combination with a cardiosurgery reservoir.

FIG. 1 depicts closed priming circuit 10 utilized in the method of the present invention. Closed priming circuit 10 includes cardiosurgery reservoir 20, which may be a combined cardiotomy and venous blood reservoir as shown. Cardiosurgery reservoir 20 generally includes venous blood inlet port 21, in fluid communication with venous inlet column 22, a plurality of cardiotomy blood inlet ports 23, in fluid communication with cardiotomy blood filter 24 and reservoir outlet 25.

In practicing the method of the present invention, cardiosurgery reservoir 20 should contain a sufficient volume of a priming solution to completely fill the internal volume of priming circuit 10 during the priming procedure. This volume will depend upon the dimensions of the blood tubing used to provide the connections between the devices described below. However, the volume will typically be in the range from about 1500 ml to about 2000 ml. The priming solution can be any type of sterile biocompatible solution used during cardiosurgery. Preferably, the priming solution is a crystalloid solution such as saline or lactated Ringer's solution. The priming solution can also contain an anticoagulant to prevent clotting and coagulation of the patient's blood during the surgical procedure as well as any other suitable additive such as albumin, mannitol and the like.

Cardiosurgery reservoir 20 may be attached to hollow fiber oxygenator heat exchanger 30 via reservoir coupling bracket 26. Alternatively, cardiosurgery reservoir 20 may be separated by some distance from combined hollow fiber oxygenator heat exchanger 30 with the understanding that reservoir outlet 25 must be higher than hollow fiber oxygenator heat exchanger 30. Whether or not cardiosurgery reservoir 20 is a combined cardiotomy and venous reservoir, it is to be understood that the individual venous and cardiotomy reservoirs must be higher than combined hollow fiber oxygenator heat exchanger 30.

Combined hollow fiber oxygenator heat exchangers are available from a variety of sources, including the wound heat exchanger oxygenator as disclosed in U.S. Pat. No. 5,429,184 to Bach et al., which is herein incorporated by reference. In particular, the method of the present invention is useful for priming hollow fiber oxygenators alone or in combination with a heat exchanger. Most oxygenators utilize a bundle of hollow fiber membranes as the conduits for oxygen flow. In outside perfusion type blood oxygenators, the oxygen flows through the lumens of the hollow fibers while the blood flows on the exteriors. Blood is oxygenated because of the oxygen concentration gradient that exists between the oxygen gas present in the hollow fiber lumens and the blood surrounding the exterior of the fiber. High oxygen transfer rates are desirable to make as much oxygen available to the patient's system as possible.

As described above, the hollow fiber oxygenator can be integrated with a blood heat exchanger. Cardiosurgery is typically performed at temperatures below the normal human body temperature (37° C.). Therefore, the perfusionist must lower the body's temperature prior to initiating the surgical procedure. The method of the present invention will be described in connection with a combined hollow fiber oxygenator heat exchanger, but it is to be understood that the method of the present invention is suitable for priming separate oxygenator and heat exchanger units.

Combined hollow fiber oxygenator heat exchanger 30 includes venous blood inlet 31 through which a patient's blood is introduced into hollow fiber oxygenator heat exchanger 30 for first temperature regulation and then gas exchange. Venous blood inlet 31 is connected via blood tubing to reservoir outlet 25 to create one half of closed priming circuit 10. Extracorporeal pump 28 is situated along the tubing connection between venous blood inlet 31 and reservoir outlet 25 wherein the tubing connection can remain in the pump raceway (not shown) of extracorporeal pump 28.

Combined hollow fiber oxygenator heat exchanger 30 includes arterial blood outlet 32 which provides passage of heat exchanged and oxygenated blood. Arterial blood outlet 32 is connected to venous inlet port 21 to create the second half of the circuit utilized in the method of the present invention. In this manner, priming circuit 10 is a closed system. Hollow fiber oxygenator heat exchanger 30 includes heat exchange media inlet 33, heat exchange media outlet 34, gas exchange media outlet 35 and gas exchange media inlet 36.

In practicing the method of the present invention, gas exchange media inlet 36 is connected to vacuum source 50 via vacuum line 51. All other inlets or access ports to both cardiosurgery reservoir 20 and hollow fiber oxygenator heat exchanger 30 must be closed in an air tight manner.

B. The Priming Method

Figure 2:
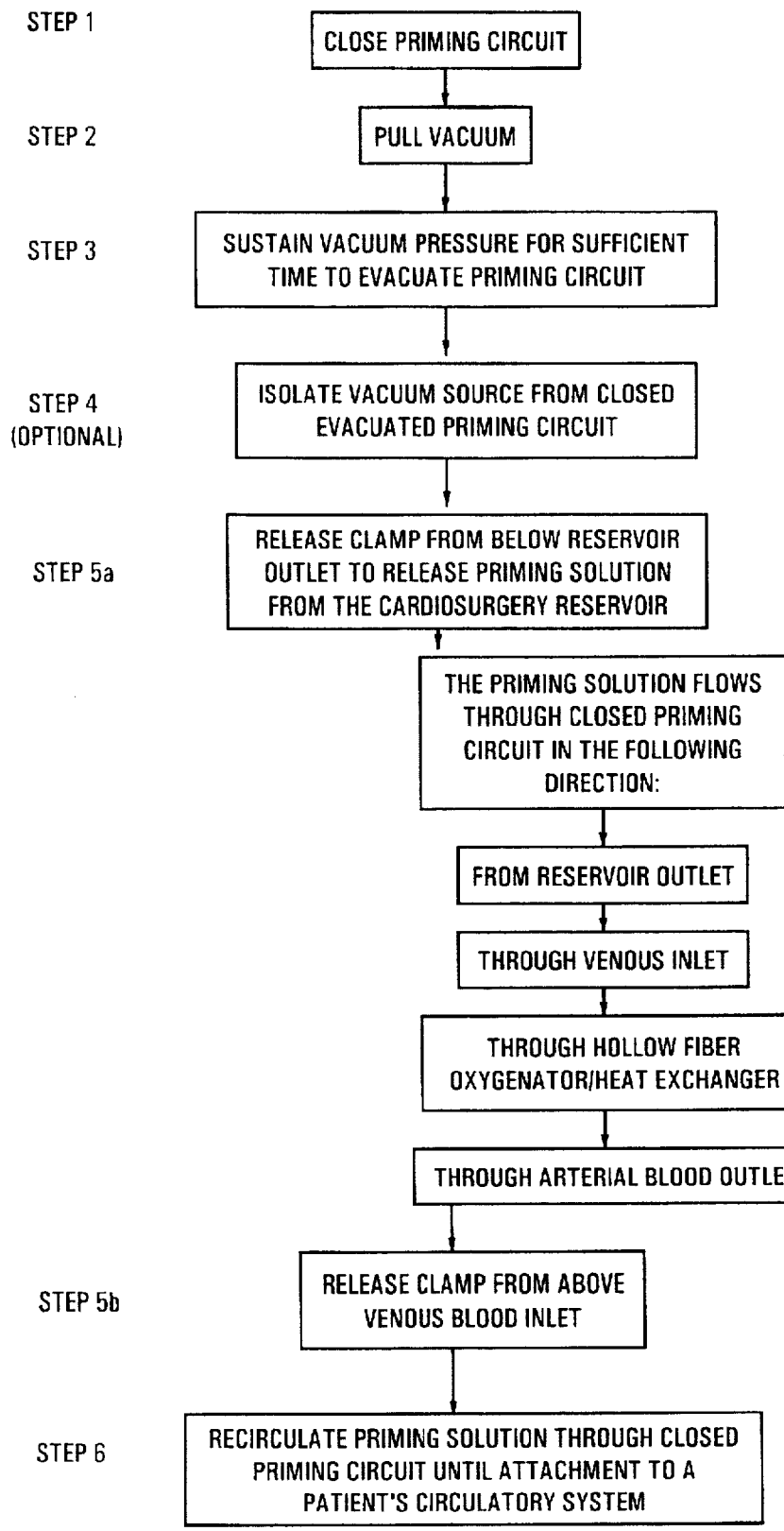
FIG. 2 is a flow diagram of the method of the present invention.

Referring to FIG. 2, Step 1 in the method of the present invention includes sealing closed priming circuit 10. This is accomplished by placing a first clamp at point 41 located just below reservoir outlet 25 and a second clap at point 42 located just above venous inlet port 21. By sealing closed priming circuit 10 with clamps in these locations, the priming solution is isolated from vacuum line 51 so that it is not pulled through closed priming circuit 10 prematurely. Preferably, the tubing which connects reservoir outlet 25 with venous blood inlet 31 is removed from the raceway of extracorporeal pump 28 during application of vacuum pressure described below. A third clamp may be provided at point 43 near gas exchange media inlet 36, the function of which will be described below.

Step 2 includes applying vacuum pressure to sealed closed priming circuit 10. Preferably, the vacuum pressure is between –200 mmHg (millimeters mercury) to –760 mmHg. More preferably, the vacuum pressure is between about –300 mmHg to about –700 mmHg.

Vacuum pressure is applied for a sufficient time to evacuate closed priming circuit 10. The time necessary for air removal is inversely proportional to the vacuum pressure applied. In other words, as the desired vacuum pressure increases, the time required for air removal decreases. Further, air removal from the closed priming circuit can be visualized by the collapse of the blood tubing forming the connections between cardiosurgery reservoir 20 and hollow fiber oxygenator heat exchanger 30. For example, at an applied vacuum pressure of about –500 mmHg, a time of about 2 minutes would be sufficient for air removal.

As stated above, vacuum source 50 is attached to gas exchange media inlet 36 which is in fluid communication with the lumen of each hollow fiber membrane within the oxygenator portion. Vacuum pressure removes air within the tubing connections, the heat exchanger portion and the oxygenator portion wherein the air passes through the membrane micropores and out through the lumen of the hollow fibers.

Once closed priming circuit 10 is evacuated, Step 4 can optionally be included for isolating vacuum source 50 from the evacuated closed priming circuit 10 by closing the clamp at point 43 so that priming solution is not drawn through to vacuum source 50. Step 5 includes releasing the priming solution from cardiosurgery reservoir 20 by removing clamp at point 41. The priming solution flows through closed priming circuit 10 due to the negative pressure created. The priming solution flows from reservoir outlet 25, through venous blood inlet 31, through hollow fiber oxygenator heat exchanger 30 and out through arterial blood outlet 32. The tubing connection between reservoir outlet 25 and venous blood inlet 31 is inserted into the pump raceway and extracorporeal pump 28 is slowing initiated. Clamp at point 42 is then opened which allows the priming solution to flow through venous inlet port 21 through venous inlet column 22 within cardiosurgery reservoir 20.

By establishing the priming solution flow path in this manner, any air which may be trapped within the blood tubing or in remote areas within hollow fiber oxygenator heat exchanger 30 is carried with the priming solution and into cardiosurgery reservoir 20. As described above, a sufficient priming solution volume must be provided so that when closed priming circuit 10 is filled with the priming solution, a residual amount remains within cardiosurgery reservoir during the priming procedure to trap any remaining air and to prevent its reintroduction into closed priming circuit 10.

Step 6 includes recirculation of the priming solution through closed priming circuit 10. This can be accomplished by slowly increasing the speed of cardiosurgery pump 28 so that the priming solution follows the path described above. Recirculation can be continued until a patient's circulatory system is attached to the extracorporeal circulatory system including cardiosurgery reservoir 20 and hollow fiber oxygenator heat exchanger 30.

While a description of the preferred embodiment has been presented, it is contemplated that various changes, including those mentioned above, could be made without deviating from the spirit of the present invention. It is therefore desired that the present embodiment be considered in all respects as illustrative, not restrictive, and that reference be made to the appended claims rather than to the foregoing description to indicate the scope of the invention.

We claim:

1. A method for priming a hollow fiber oxygenator heat exchanger comprising:
    (a) creating a closed priming circuit within an extracorporeal circuit wherein (i) a cardiosurgery reservoir outlet is in fluid communication with a venous blood inlet of a hollow fiber oxygenator heat exchanger, and (ii) an arterial blood outlet of said hollow fiber oxygenator heat exchanger is in fluid communication with a blood inlet port of a cardiosurgery reservoir;
    (b) providing a sufficient volume of a priming fluid in said cardiosurgery reservoir to fill an internal volume of said closed priming circuit;
    (c) providing a vacuum source to a gas inlet of said hollow fiber oxygenator heat exchanger;
    (d) applying a vacuum pressure to said closed priming circuit for a sufficient amount of time creating an evacuated closed priming circuit;
    (e) releasing said priming fluid within the cardiosurgery reservoir to thereby prime said evacuated closed priming circuit; and
    (f) recirculating said priming solution through said closed priming circuit until attachment of said extracorporeal circuit to a patient's circulation system.

2. The method for priming a hollow fiber oxygenator heat exchanger according to claim 1 further comprising sealing said closed priming circuit isolating said cardiosurgery reservoir wherein (i) a first clamp is located between said cardiosurgery reservoir outlet and said venous blood inlet of said hollow fiber oxygenator heat exchanger, and (ii) a second clamp is located between said arterial blood outlet of said hollow fiber oxygenator heat exchanger and said blood inlet port of said cardiosurgery reservoir.

3. The method for priming a hollow fiber oxygenator heat exchanger according to claim 2, wherein releasing said priming fluid further comprises (i) removing said first clamp between said cardiosurgery reservoir outlet and said venous blood inlet of said hollow fiber oxygenator heat exchanger, and (ii) removing said second clamp between said arterial blood outlet of said hollow fiber oxygenator heat exchanger and said blood inlet port of said cardiosurgery reservoir.

4. The method for priming a hollow fiber oxygenator heat exchanger according to claim 1 wherein said vacuum pressure of step (d) is between about −200 mmHg and −760 mmHg.

5. The method for priming a hollow fiber oxygenator heat exchanger according to claim 1 wherein said sufficient amount of time of step (d) is at least about 2 minutes.

6. The method for priming a hollow fiber oxygenator heat exchanger according to claim 1 further comprising attaining a desired vacuum pressure prior to applying said vacuum pressure to said closed priming circuit.

7. The method for priming a hollow fiber oxygenator heat exchanger according to claim 6 wherein said desired vacuum pressure is between about −200 mmHg and −760 mmHg.

8. The method for priming a hollow fiber oxygenator heat exchanger according to claim 7 further comprising isolating said vacuum source from said evacuated closed priming circuit prior to releasing said priming fluid with said cardiosurgery reservoir.

* * * * *